(12) United States Patent
Chen

(10) Patent No.: US 11,360,058 B2
(45) Date of Patent: Jun. 14, 2022

(54) METHOD AND DEVICE FOR CHEMICAL QUANTIFICATION USING ELECTROCHEMICAL MASS SPECTROMETRY WITHOUT THE USE OF STANDARD TARGET COMPOUNDS

(71) Applicant: Ohio University, Athens, OH (US)

(72) Inventor: Hao Chen, The Plains, OH (US)

(73) Assignee: Ohio University, Athens, OH (US)

( * ) Notice: Subject to any disclaimer, the term of this patent is extended or adjusted under 35 U.S.C. 154(b) by 716 days.

(21) Appl. No.: 16/341,622

(22) PCT Filed: Oct. 25, 2017

(86) PCT No.: PCT/US2017/058230
§ 371 (c)(1),
(2) Date: Apr. 12, 2019

(87) PCT Pub. No.: WO2018/081228
PCT Pub. Date: May 3, 2018

(65) Prior Publication Data
US 2021/0333248 A1    Oct. 28, 2021

Related U.S. Application Data

(60) Provisional application No. 62/413,669, filed on Oct. 27, 2016.

(51) Int. Cl.
*G01N 30/72* (2006.01)
*G01N 30/86* (2006.01)
(Continued)

(52) U.S. Cl.
CPC ......... *G01N 30/72* (2013.01); *G01N 30/8679* (2013.01); *G01N 33/6848* (2013.01); *G01N 2030/8831* (2013.01); *G01N 2560/00* (2013.01)

(58) Field of Classification Search
None
See application file for complete search history.

(56) References Cited

U.S. PATENT DOCUMENTS

| 2010/0258717 A1 | 10/2010 | Chen et al. |
| 2013/0023005 A1 | 1/2013 | Chen et al. |
| 2015/0288013 A1 | 10/2015 | Chen et al. |

OTHER PUBLICATIONS

International Search Report and Written Opinion in International Patent Application No. PCT/US2017/058230, dated Jan. 5, 2018, 8 pgs.

(Continued)

*Primary Examiner* — Xiaoyun R Xu
(74) *Attorney, Agent, or Firm* — Wood Herron & Evans LLP

(57) ABSTRACT

A method of quantifying a target compound includes applying an oxidation/reduction potential to an electrochemical cell (14); measuring an electrochemical current during the application of the oxidation/reduction potential; and ionizing and directing the target compound before and after the application of the oxidation/reduction potential to a mass spectrometer (16) that measures a target compound ion intensity. The method further includes determining a target compound ion intensity change due to the application of the oxidation/reduction potential and determining a total amount of the target compound in the sample using the measured electrochemical current and the target compound ion intensity change. Determining the target compound ion intensity change may comprise either comparing the target compound ion intensity before and after the electrolysis relative to a reference peak or comparing the integrated peak area of a target compound ion in an extracted ion chromatogram before and after the electrolysis.

19 Claims, 17 Drawing Sheets

(51) Int. Cl.
*G01N 33/68* (2006.01)
*G01N 30/88* (2006.01)

(56) References Cited

OTHER PUBLICATIONS

Li, Jiwen et al., "Online Coupling of Electrochemical Reactions with Liquid Sample Desorption Electrospray Ionization-Mass Spectrometry," Analytical Chemistry, Dec. 2009, pp. 9716-9722, vol. 81, No. 23, American Chemical Society.

Miao, Zhixin et al., "Direct Analysis of Liquid Samples by Desorption Electrospray Ionization-Mass Spectrometry (DESI-MS)," American Society for Mass Spectrometry, Sep. 2008, pp. 10-19, vol. 20, Elsevier Inc.

A: GIVEQCCASVCSLYQLENYCN
B: FVNQHLCGSHLVEALYLVCGERGFFYTPKT

INSULIN

→ PEPSIN DIGESTION →

GIVEQCCASVCSL
FVNQHLCGDHL

PEPTIDE 1

→ TCEP REDUCTION →

FVNQHLCGDHL

PEPTIDE 2

METHOD AND DEVICE FOR CHEMICAL QUANTIFICATION USING ELECTROCHEMICAL MASS SPECTROMETRY WITHOUT THE USE OF STANDARD TARGET COMPOUNDS

CROSS-REFERENCE TO RELATED APPLICATION

This application claims the benefit of U.S. Provisional Patent Application No. 62/413,669, filed on Oct. 27, 2016, the disclosure of which is incorporated herein by reference in its entirety.

STATEMENT REGARDING FEDERALLY SPONSORED RESEARCH OR DEVELOPMENT

This invention was made with government support under NSF CHE-1149367 awarded by the National Science Foundation. The government has certain rights in the invention.

BACKGROUND

Quantification is of great significance for any chemical measurements. Mass spectrometry (MS) has become a widely used technique for characterization and identification of both small and large molecules due to its capability for determining molecular weight (MW) and molecular structure based on tandem mass analysis. Although MS is powerful in qualitative analysis, accurate quantification by MS has challenges because the MS signal fluctuates and the signal intensity in a MS spectrum does not always correlate well with the amount of the target analyte in the sample. Therefore, accurate quantification MS methods often rely on the use of standard compounds for calibration or employing isotope-labeled compound as a reference. However, the chemical standard is often not commercially available or is difficult to synthesize (e.g., drug metabolites or proteins in cells). It is therefore necessary to develop a new technique that is highly sensitive and selective for accurate chemical quantification and does not need standard compounds.

SUMMARY

Embodiments of the present invention are directed to methods and devices for chemical quantification using mass spectrometry (MS) combined with electrochemistry (EC). In one embodiment, the device includes a liquid chromatography (LC), an electrochemical cell (EC), and a mass spectrometer. With the LC, the device may be used for the analysis of mixture samples, such as clinic samples. If the analysis is for a purified sample, the LC may be excluded. A target compound in mixture is subjected to LC separation, followed by electrochemical oxidation or reduction in the electrochemical cell and online MS detection. Both the redox current and the response of MS spectra are recorded. The MS provides the percentage of analyte that is oxidized/reduced, and the EC current information reveals how much analyte is oxidized/reduced, thus allowing the quantification of the amount of the target compound present in the sample. Advantageously, this quantification method does not involve the use of standard compounds and is applicable for analysis of target compounds in a complex mixture. Therefore, it is of high value particularly where the chemical standard is not commercially available or is difficult to synthesize (e.g., drug metabolites or proteins). This method has a wide scope of applications and would be also applicable to the analysis of both small organic molecules and large biomolecules, such as proteins and DNA.

The objects and advantages of the present invention will be further appreciated in light of the following detailed description and drawings provided herein.

BRIEF DESCRIPTION OF THE DRAWINGS

The accompanying drawings, which are incorporated in and constitute a part of this specification, illustrate embodiments of the invention and, together with a general description of the invention given above and the detailed description given below, serve to explain the principles of the invention.

DETAILED DESCRIPTION

Embodiments of the present invention are directed to quantification methods and electrochemical mass spectrometry devices. In an aspect of the present invention, it is advantageous that no calibration against a chemical standard is required. Furthermore, methods of chemical quantification described herein are highly sensitive due to the inherent high sensitivity of mass spectrometry and electrochemistry. As shown below, samples containing pmols of the target compound can be directly quantified. The target compounds may include, without limitation, small organic molecules and large biomolecules, such as proteins, drug metabolites, and DNA. Such methods are beneficial in a wide scope of potential applications. For example, potential applications include use by pharmaceutical companies, biotechnical companies, environmental agencies, and instrument companies.

Figure 1:
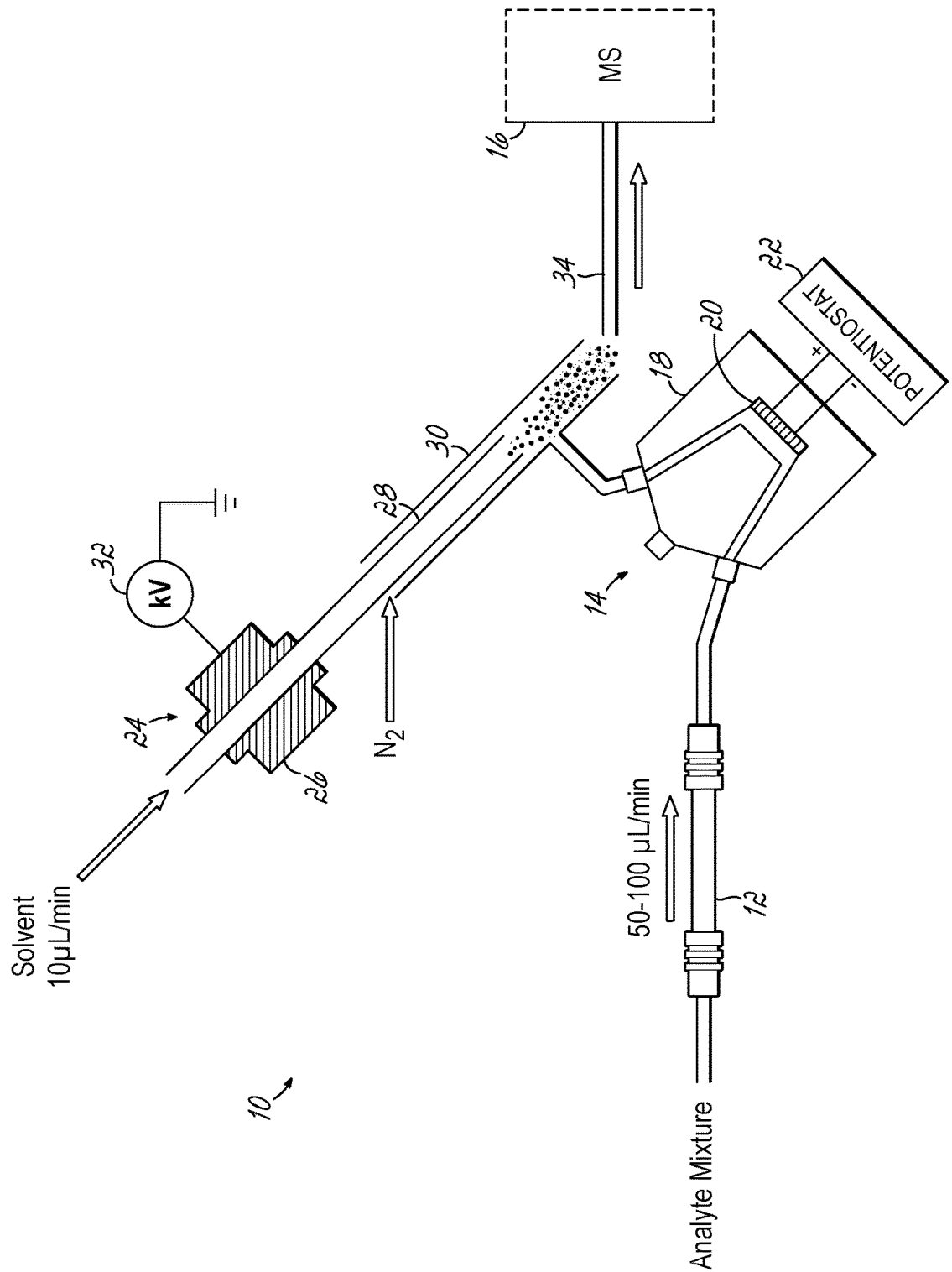
FIG. 1 is a diagrammatic cross-sectional view of an electrochemical mass spectrometry device according to an embodiment of the present invention.

With reference to FIG. 1, in an embodiment, an electrochemical mass spectrometry device 10 includes a liquid chromatography (LC) instrument 12, an electrochemical cell 14, and a mass spectrometer 16. Liquid chromatography is utilized to separate the target compound from an analyte mixture and is directly connected with the electrochemical cell 14 and further connected with the downstream mass spectrometer 16. In one embodiment, the LC instrument 12 performs ultra-performance liquid chromatography (UPLC). It should be noted that other types of liquid chromatography can be used as well. The electrochemical cell 14 includes a reaction chamber 18 that contains at least one electrode 20. For example, the electrochemical cell 14 may include a working electrode (WE), a reference electrode, and an auxiliary electrode. When the LC eluent flows through the electrochemical cell 14, an oxidation/reduction potential is applied by a potentiostat 22 so that the LC-separated compounds undergo electro-oxidation/electro-reduction. During the application of the oxidation/reduction potential, the oxidation/reduction current responses are monitored and recorded by the potentiostat 22 or another sensor. Meanwhile, the resulting oxidized/reduced products, along with unreacted compounds, are ionized and then detected by the mass spectrometer 16. The mass spectrometer 16 measures an intensity of the ionized target compound ion (i.e., a target compound ion intensity) both before and after the application of the oxidation/reduction potential to the target compound in the electrochemical cell 14.

With further reference to FIG. 1, in one embodiment, a liquid sample desorption electrospray ionization (DESI) system 24 is used as the ionization method to couple the electrochemical cell 14 with the mass spectrometer 16. The DESI system 24 generates charged microdroplets of a chosen solvent and directs the charged microdroplets toward the oxidized/reduced products from the electrochemical cell 14. The DESI system 24 includes a housing 26 having a solvent conduit 28 for solvent surrounded by a gas conduit 30. A voltage generator 32 is attached to the housing 26 and is operable to charge the solvent within the solvent conduit 28. The spray impact of the charged solvent microdroplets with the oxidized/reduced products ionizes and deflects an ionized portion of the oxidized/reduced products into the mass spectrometer 16. The mass spectrometer 16 has a sample entrance or opening 34, such as a heated capillary. A suitable DESI system is described in U.S. Patent Application Publication No. 2015/0288013, the disclosure of which is incorporated herein by reference in its entirety. While the illustrated embodiment includes a DESI system, any soft ionization methods including electrospray ionization (ESI), atmospheric pressure chemical ionization (APCI), and matrix-assisted laser desorption ionization (MALDI), or other ambient ionization methods based on impact by high energy particles, such as laser or plasma, can be used for this purpose as well.

Figure 2:
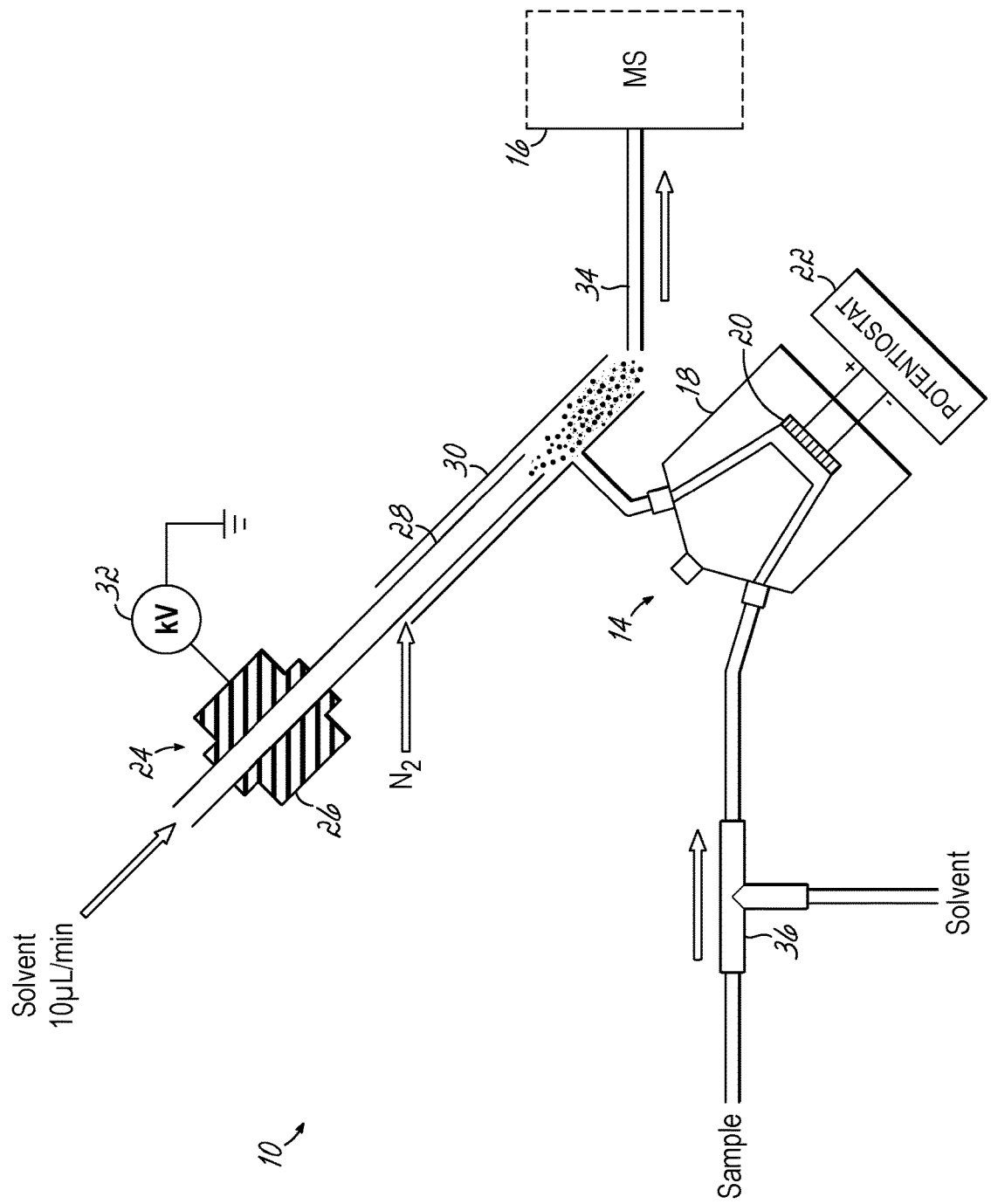
FIG. 2 is a diagrammatic cross-sectional view of an electrochemical mass spectrometry device according to another embodiment of the present invention.

With reference to FIG. 2, in an embodiment where the target compound is sufficiently purified, an electrochemical mass spectrometry device 10' excludes the LC instrument 12. In such an embodiment, a solvent flow may be injected into the electrochemical cell, for example, via a Tee mixer 36 to establish an oxidation/reduction current baseline. Then a sample may be injected as a pulse to the electrochemical cell 14 to trigger the formation of an oxidation/reduction current for recording.

To calculate the total amount of the target compound in the sample, the percentage of the target compound that is oxidized/reduced is first calculated using the mass spectrometry data as described below. Additionally, the amount of the target compound that is oxidized/reduced is determined based on the electrochemical response. The recorded EC current peak reveals how much of a target compound is oxidized/reduced by the integration of the recorded current peak against time, based on Faraday's Law (i.e., $n=Q/zF$ where Q is the consumed electricity, n is the number of moles of compounds that are oxidized/reduced in the electrochemical reaction, Z is the number of electrons involved in the electrochemical reaction per molecule, and F is the Faraday's constant, $9.65\times10^4$ C/mol). The information from both MS and EC measurements can be used to calculate the amount of target compound as shown below.

$$A = A_{o/r}/(\% \text{ of the target compound that is oxidized/reduced}) \quad \text{(Eq. 1)}$$
$$= A_{o/r}/(\text{the target compound ion intensity change}\%)$$

where A is the total amount of the target compound in the sample, and $A_{o/r}$ is the amount of the target compound that was oxidized/reduced ($A_{o/r}=n$).

Figure 3:
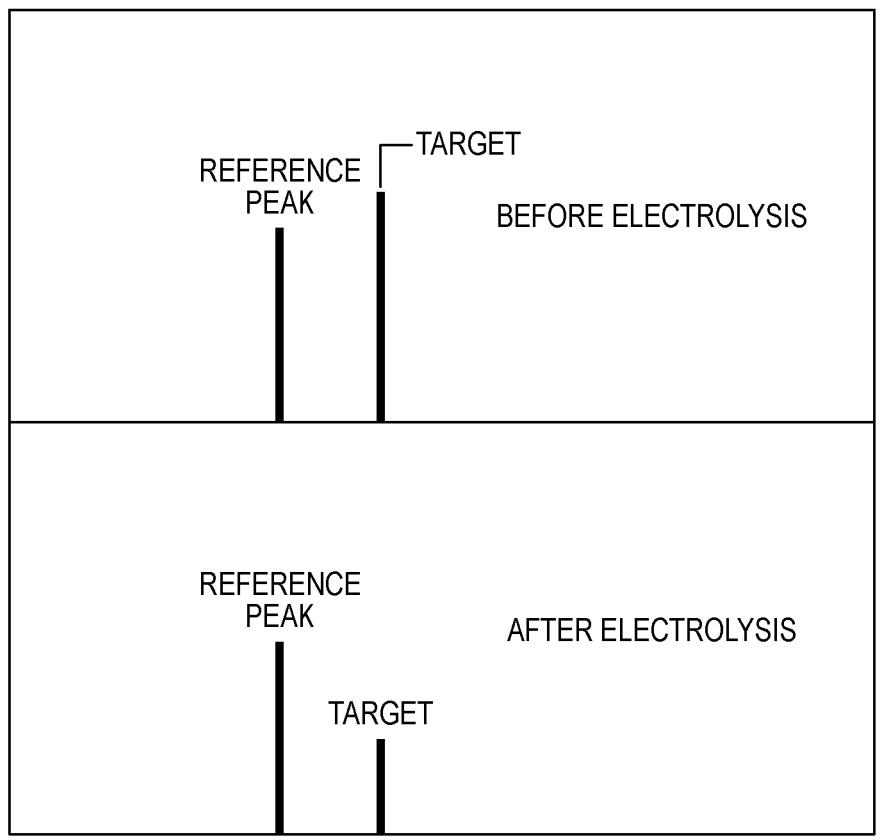
FIG. 3 shows a method of calculating the oxidation/reduction yield of the target compound according to an embodiment of the present invention using the comparison of the target compound that is oxidized/reduced with a reference compound peak before and after electrolysis, respectively.

With reference to FIG. 3, in an embodiment, the percentage of the target compound that is oxidized/reduced is calculated using the target compound ion relative intensity change (relative to a ion intensity peak of a chosen reference compound). The mass spectrometer measures the ion intensity of the reference compound. The MS data provides information about the percentage of analyte that was oxidized/reduced based on the relative ion intensity change before and after electrolysis in comparison to the ion intensity of the reference compound peak. Note, the reference compound can be any compound that has a mass signal close to the target compound ion. In addition, the reference compound is not oxidized/reduced under the oxidation potential applied to oxidize/reduce the target compound and has no contribution to the current response.

Figure 4A:
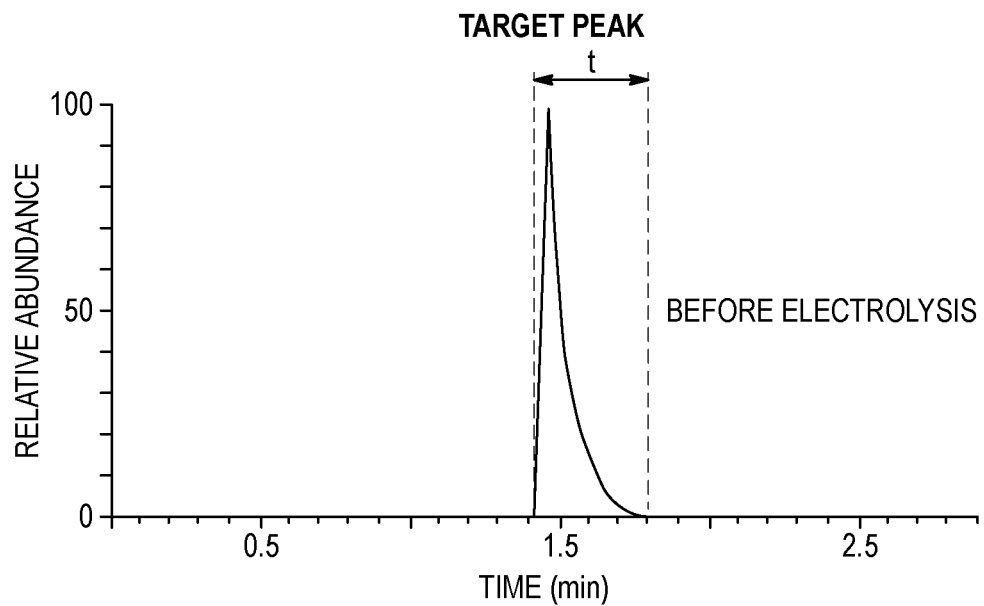
FIGS. 4A and 4B are graphs showing a method of calculating the oxidation/reduction yield of target compound according to another embodiment of the present invention using a change in the extracted ion chromatogram (EIC) peak integrated area before and after electrolysis, respectively.
Figure 4B:
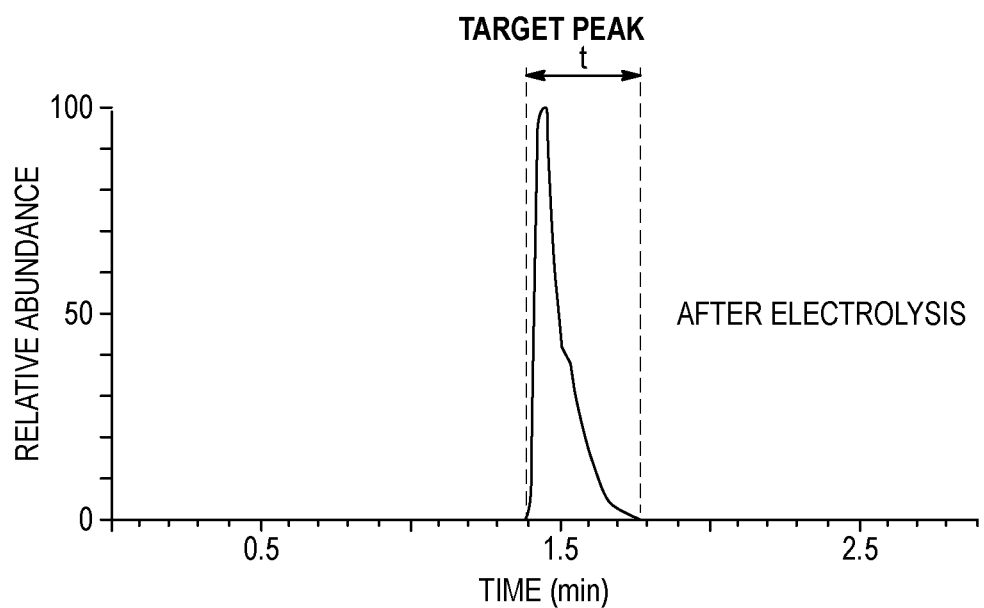

With reference to FIGS. 4A and 4B, in an embodiment, the percentage of the target compound that is oxidized/reduced is calculated based on the change in the integrated peak area for the target compound in the extracted ion chromatograms (EICs) before and after electrolysis. Accordingly, there is no need to use any reference compound. The integration window (t) is kept the same before and after electrolysis.

In order to facilitate a more complete understanding of the embodiments of the invention, the following non-limiting examples are provided.

Quantification for target compound analysis. In an embodiment, the quantification method is used to analyze a solution containing a target compound that is electrochemically oxidizable or reducible.

Example 1

Setup. A Waters UPLC (Milford, Mass., USA) equipped with a C18 column was coupled with an electrochemical cell. The electrochemical cell employed a glassy carbon (GC) electrode as the working electrode (WE), a platinum electrode as the reference electrode, and titanium as the auxiliary electrode. A positive potential ranging from +1.2 to +1.3 V was applied to the WE electrode for oxidation of the eluent from the UPLC. The oxidation current response was monitored and recorded by using a potentiostat.

The resulting oxidized/reduced products were then ionized by a home-built modified DESI source and analyzed by Waters QTOF. The DESI source includes a PEEK tube with a micro-drilled sample inlet, which allows mixing of the sprayed and charged microdroplets with the sample flowing out of the electrochemical cell, which is introduced via a piece of sample transfer capillary (e.g., see FIGS. 1 and 2). The mixing results in ionization of the sample for MS detection. A mixture of MeOH:H$_2$O (1:1 by volume) containing 1% formic acid (FA) was used as the spray solvent and sprayed at a flow rate of 10 µL/min.

Dopamine, norepinephrine, and rutin samples were analyzed. For dopamine and norepinephrine separation, a gradient elution program was used from 98% A down to 92% A in 10 min (mobile phase A: water; and mobile phase B: acetonitrile; and both containing 0.1% formic acid). For rutin separation, a gradient elution program was used from 95% A down to 60% A in 5 min.

Arginine was added in the mobile phase A at the concentration of 0.0010 g/L as the reference compound to provide the relative intensity change of target compound ion before and after electrolysis. The mobile phase flow rate was adjusted ranging from 0.050 mL/min to 0.300 mL/min. The sample injection volume varied from 3-5 µL, and the sample concentration was 50-100 µM.

Results. Table 1 below shows the experimental results for dopamine, norepinephrine, and rutin.

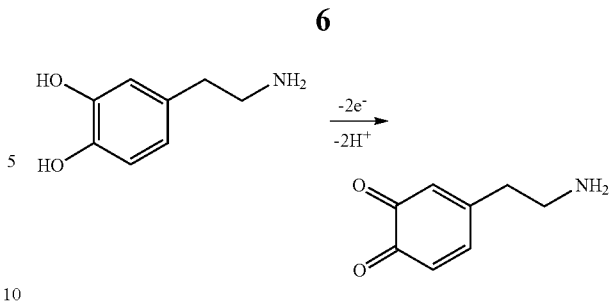

Figure 5A:
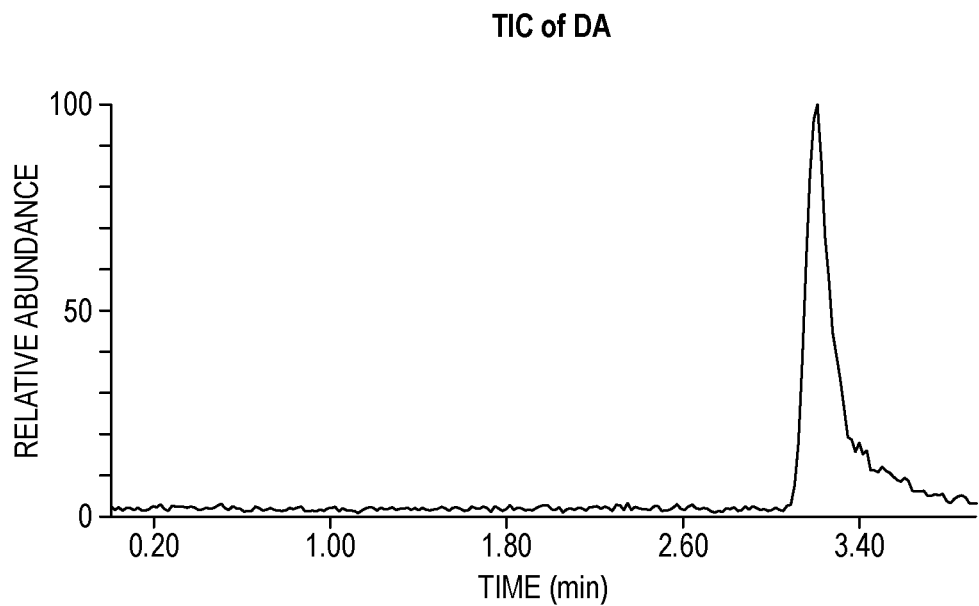
FIG. 5A is a total ion chromatogram of dopamine separation.
Figure 5B:
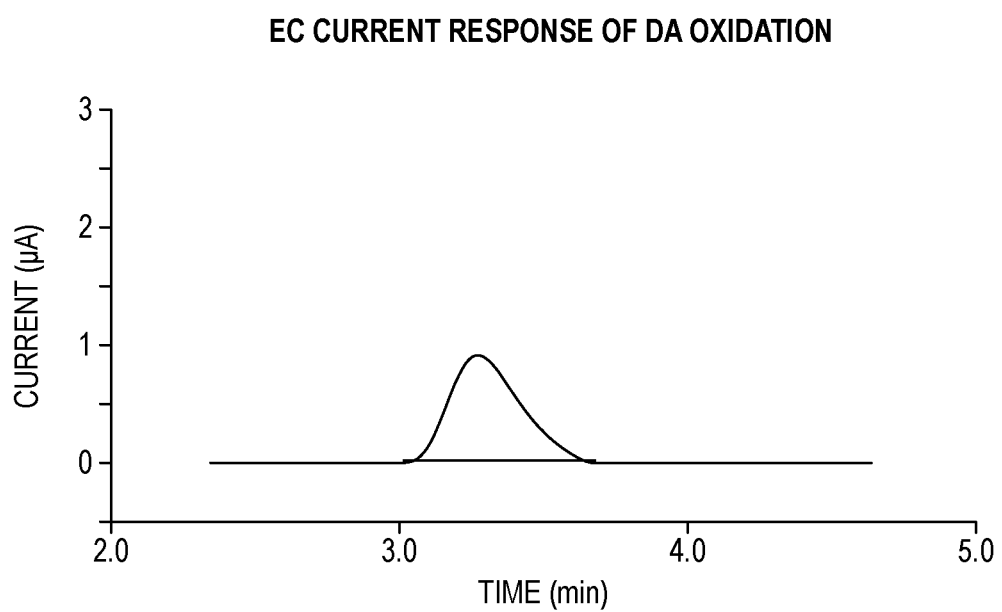
FIG. 5B is a graph showing the electrochemical current response due to dopamine oxidation.
Figure 5C:
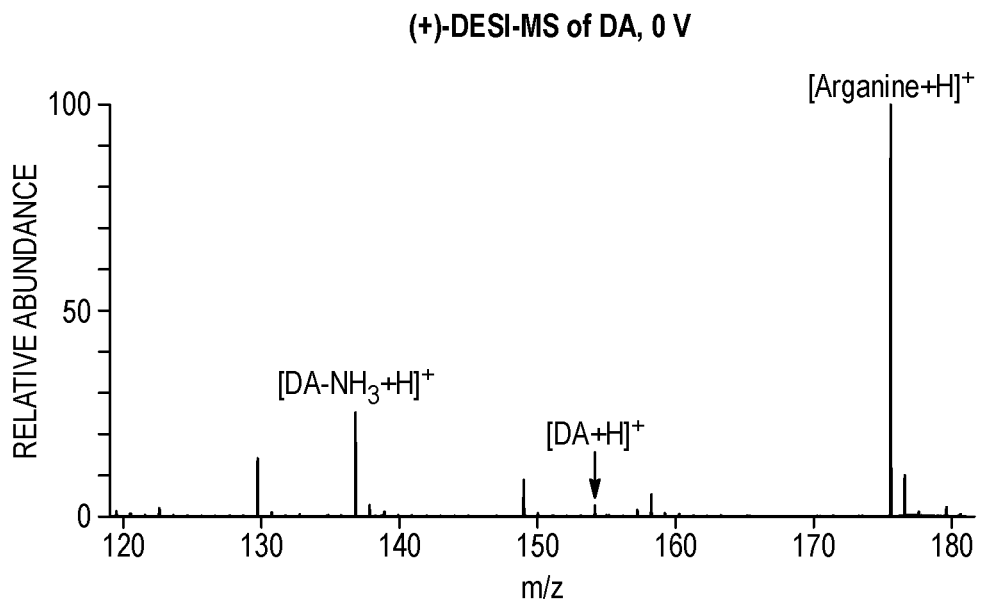
FIGS. 5C and 5D are the (+)-DESI mass spectra of dopamine with an applied potential of 0 V and +1.3 V, respectively.
Figure 5D:
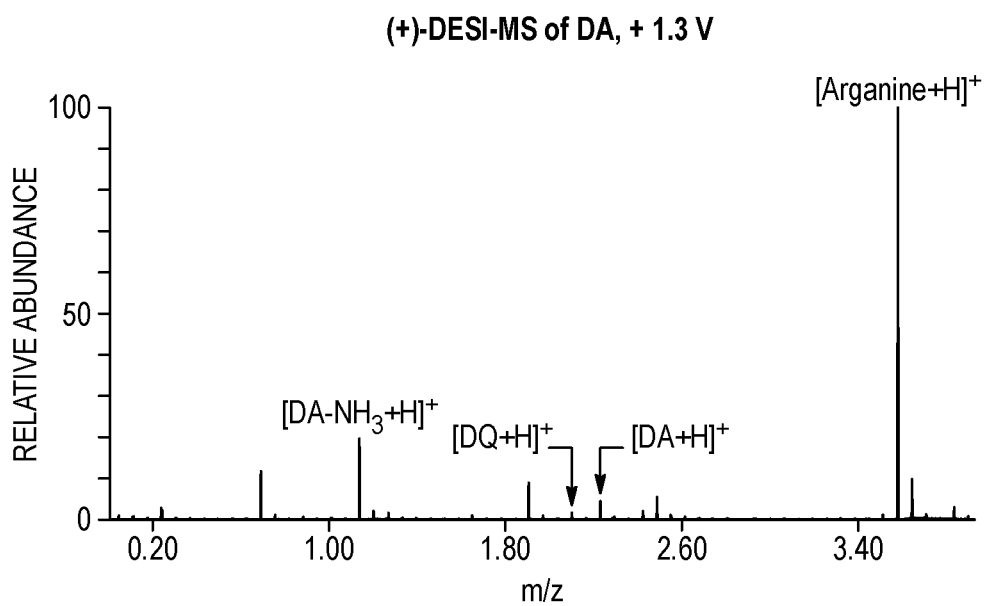

DA was dissolved in water containing 0.1% FA at the concentration of 50 µM. The sample was injected into the UPLC instrument with an injection volume of 3 µL. The mobile phase flow rate was 0.050 mL/min, and DA was eluted out at 3.0 min FIG. 5A shows the total ion chromatogram (TIC) of the dopamine separation, and FIG. 5B shows the electrochemical current response due to DA oxidation. FIGS. 5C and 5D show the acquired MS spectrum (DESI spectra) when applied potential was 0 V and +1.3 V, respectively.

The protonated arginine and the protonated DA were detected at m/z 175 and 154, respectively. Another ion appeared at m/z 137, corresponding to [DA-NH$_3$+H$^+$] due to ammonia loss from m/z 154. With an applied potential of +1.3 V, only DA was oxidized and the product dopamine quinone was detected at m/z 123 (FIG. 5D). The addition of arginine in the mobile phase would not affect the separation efficiency and the retention time of the target compound. In addition, arginine was not oxidized under the oxidation potential of +1.3 V and had no contribution to the current response of DA by observing similar current peaks generated with or without addition of arginine.

Moreover, by examining the recorded EC current response, a sharp peak was generated, which corresponded to the oxidation of dopamine (FIG. 5B). The peak area was integrated by importing data point to the potentiostat software to determine the amount of dopamine that was oxidized (FIG. 5B). The relative intensity change of dopamine before and after oxidation was measured using the protonated arginine at m/z 175.1 as the reference peak. All measurements were repeated three times and averaged values were used for calculation. The data is summarized in Table 1 above. By integrating the measured current peak areas, the calculated amount of the oxidized dopamine was

TABLE 1

|  | Dopamine | Norepinephrine | Rutin |
| --- | --- | --- | --- |
| Theoretical amount of target compound (pmol) | 150 | 300 | 500 |
| Amount of target compound oxidized/reduced (pmol) based on current | 23.29 | 24.74 | 19.50 |
| Standard Deviation | 1.41 | 1.47 | 0.33 |
| Intensity change measured by MS (%) | 14.85 | 8.12 | 3.69 |
| Standard Deviation | 0.80 | 0.64 | 0.14 |
| Measured amount of target compound* (pmol) | 156.82 | 304.56 | 528.08 |
| Standard Deviation | 12.72 | 30.00 | 22.16 |
| Error** (%) | 4.54 | 1.52 | 5.62 |

*Measured amount of the target compound (pmol) = amount of the target compound that was oxidized/reduced (pmol)/intensity change (%)
**Error (%) = (actual amount − theoretical amount)/(theoretical amount × 100%)

Dopamine. As shown below, dopamine (DA), which is an electroactive species, undergoes electrochemical oxidation via a two electron transfer reaction. Upon electrochemical oxidation, dopamine (MW 153.2) is oxidized to dopamine quinone (DQ; MW 151.2) by losing two H atoms.

23.29 pmol and the relative intensity change for DA (based on the DA fragment peak at m/z 137) was 14.85%, which tells the measured amount for DA to be 156.82 pmol. In comparison to the actual injection amount of DA (150 pmol), the measurement error is small (4.54%).

Norepinephrine. As shown below, norepinephrine (NE), which is one of the analogs of DA, undergoes electrochemical oxidation via a two electron transfer reaction. After electrochemical oxidation, norepinephrine (MW 169.2) is oxidized to norepinephrine quinone (NQ; MW 167.2).

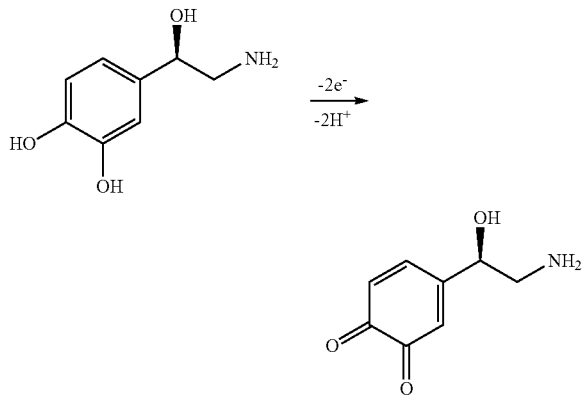

Figure 6A:
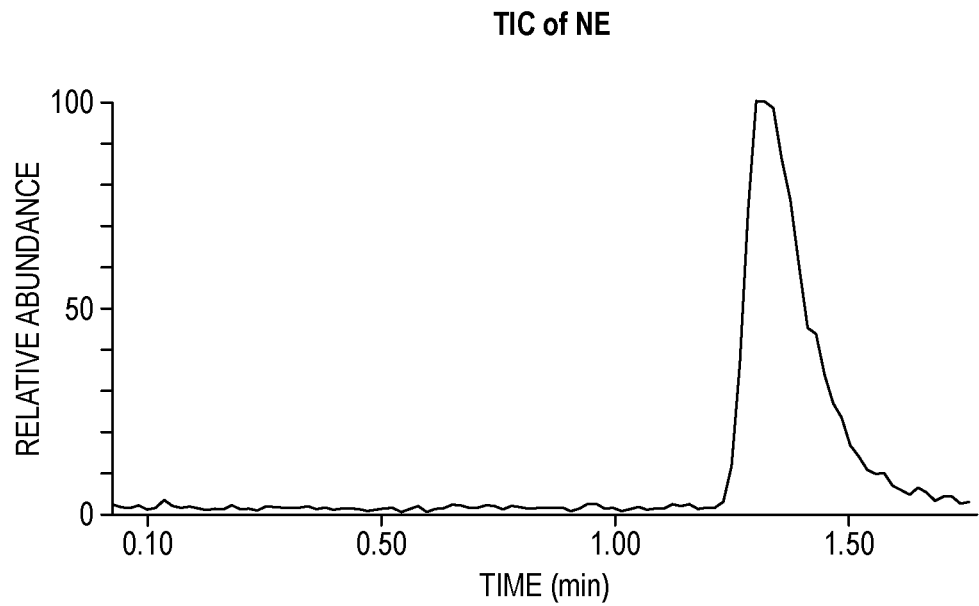
FIG. 6A is a total ion chromatogram of norepinephrine separation.
Figure 6B:
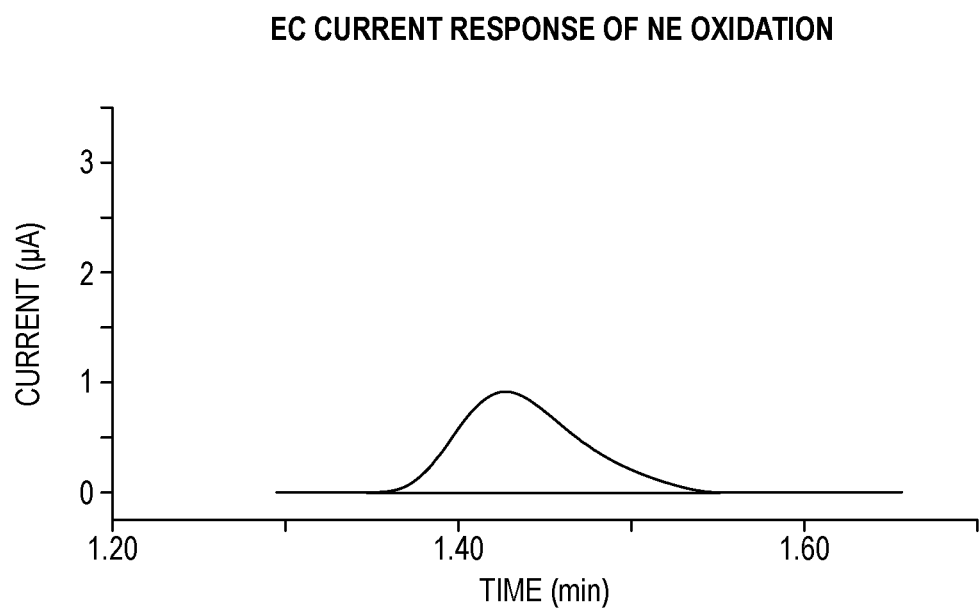
FIG. 6B is a graph showing the electrochemical current response due to norepinephrine oxidation.
Figure 6C:
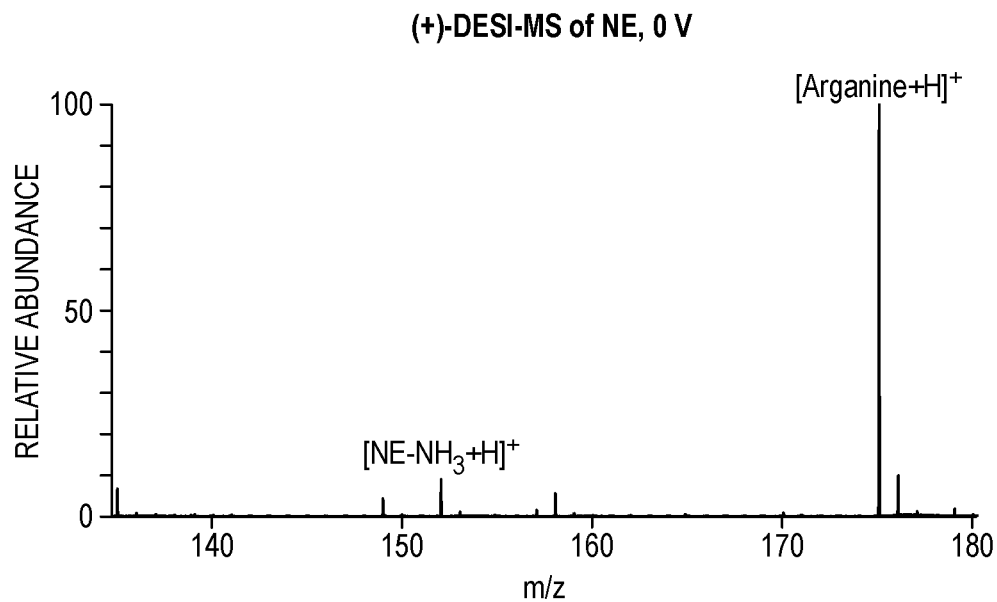
FIGS. 6C and 6D are the (+)-DESI mass spectra of norepinephrine with an applied potential of 0 V and +1.3 V, respectively.
Figure 6D:
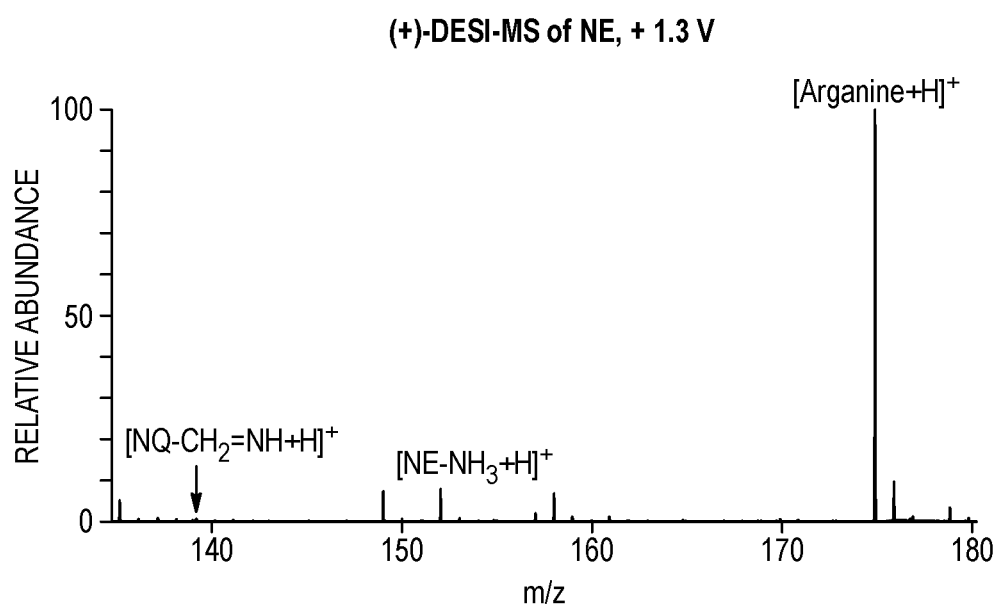

NE was dissolved in water containing 0.1% FA at concentration of 100 μM. The sample was injected into the UPLC instrument with an injection volume of 3 μL. The mobile phase flow rate of 0.100 mL/min, and the NE was eluted out at 1.25 min. FIG. 6A shows that the TIC of the NE separation, and FIG. 6B shows the EC current response due to NE oxidation. FIGS. 6C and 6D show the acquired MS spectrum (-DESI spectra) when the applied potential was 0 V and +1.3 V, respectively. Besides the protonated arginine (m/z 175), a fragment ion of NE, [NE-NH$_3$+H$^+$], was detected at m/z 152 due to the loss of ammonia. With an applied potential of +1.3 V, the oxidized product of NE was detected at m/z 139, while arginine was not affected (FIG. 6D). The measurement of EC current response and the relative ion intensity change for m/z 152 are summarized in Table 1. The amount of oxidized NE was calculated as 24.74 pmol, and the relative intensity drop was 8.12%, which shows the measured amount of NE to be 304.56 pmol. The measurement error is only 1.52%, which is low in consideration of the actual NS injection amount of 300 pmol.

Rutin. As shown below, rutin, which is a glycoside of the flavonoid quercetin containing two glycol units, undergoes electrochemical oxidation via a two electron transfer reaction at the 3' and 4' phenol groups. Upon electrochemical oxidation, rutin (MW 610.5) is oxidized to ketone (MW 608.5) by losing two H atoms.

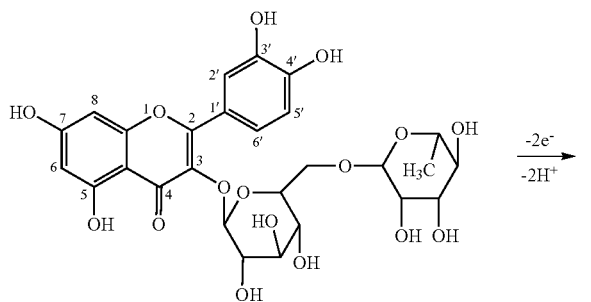

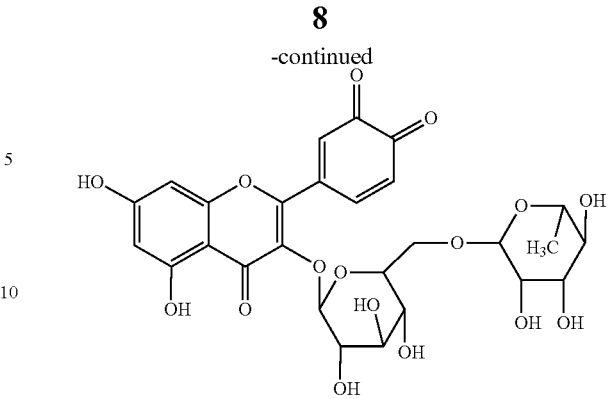

Figure 7A:
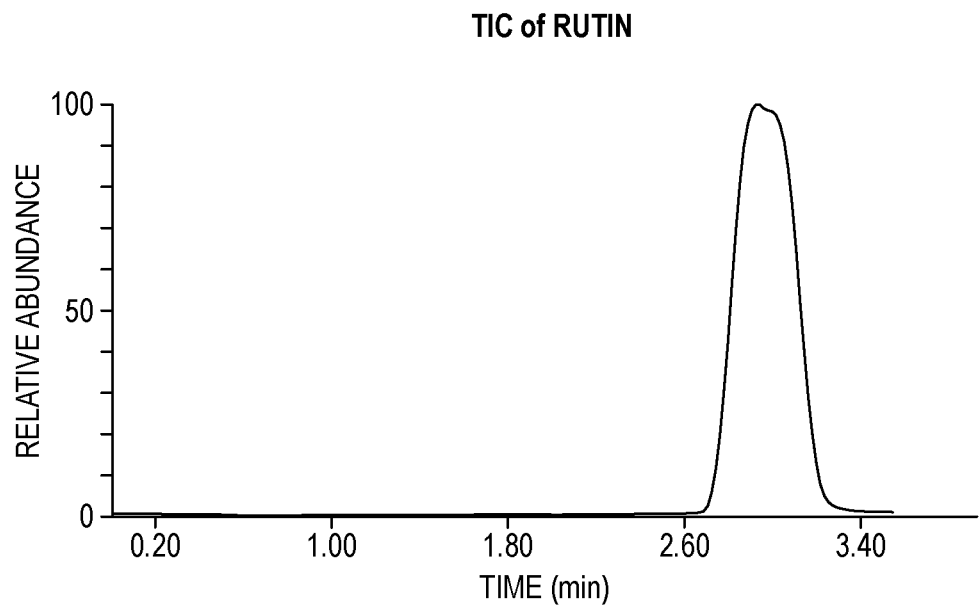
FIG. 7A is a total ion chromatogram of rutin separation.
Figure 7B:
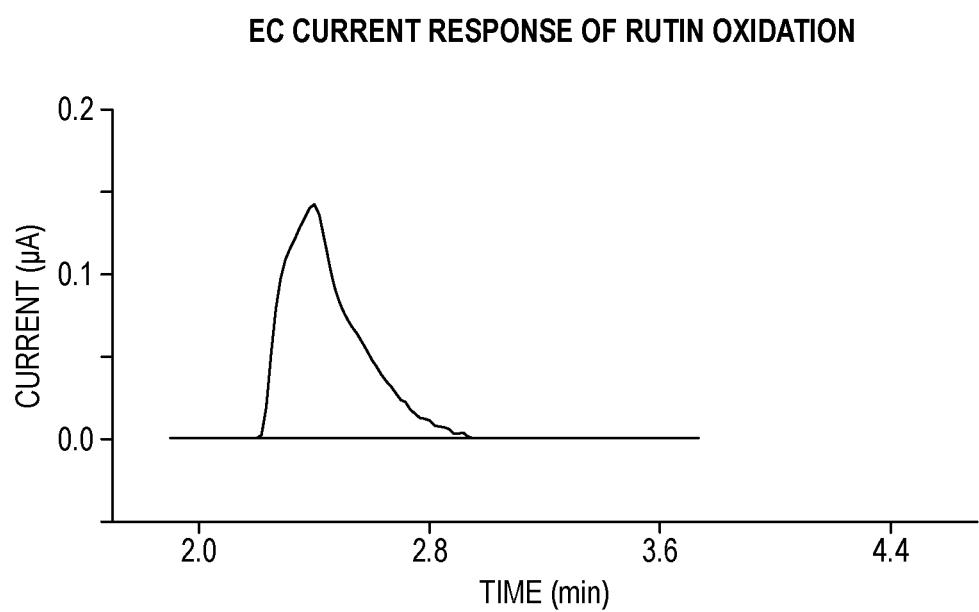
FIG. 7B is a graph showing the electrochemical current response due to rutin oxidation.
Figure 7C:
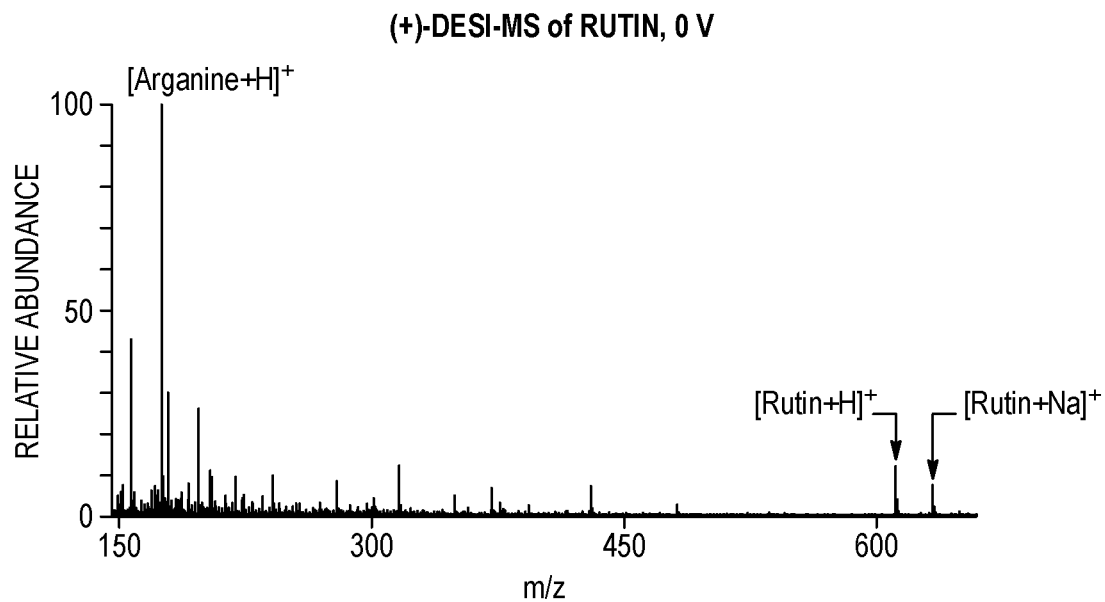
FIGS. 7C and 7D are the (+)-DESI mass spectra of rutin with an applied potential of 0 V and +1.2 V, respectively.
Figure 7D:
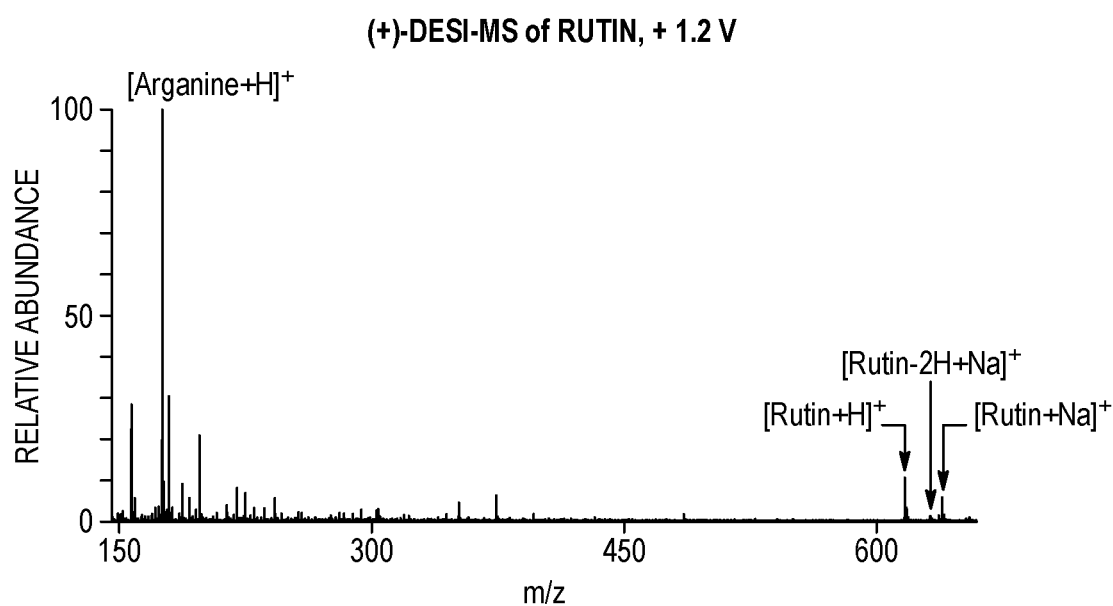

Rutin was first dissolved in dimethyl sulfoxide and diluted by water containing 0.1% formic acid to the final concentration of 100 μM. The sample was injected into the UPLC instrument with an injection volume of 5 μL at the flow rate of 0.300 ml/min. FIG. 7A is the TIC of the rutin separation. FIG. 7B shows the EC current response due to rutin oxidation. FIGS. 7C and 7D show the acquired MS spectrum (DESI spectra) when applied potential was 0 V and +1.3 V, respectively.

Only the protonated rutin was detected at m/z 611.2 and its sodium adduct at m/z 633.2. With an applied oxidation potential of +1.2 V, the oxidized product of rutin was detected at m/z 631.2 (FIG. 7D). The measurement comparison between EC current response and MS is summarized in Table 1. In the recorded EC current response, one current peak appears at 2.5 min, corresponding to the rutin oxidation. The peak at 2.5 min was integrated by importing the data to software to determine the amount of rutin that was oxidized (FIG. 7B). The data is summarized in Table 1 above. Based on the integration of the peak area, the amount of the oxidized rutin was calculated to be 19.50 pmol. Furthermore, the relative rutin intensity change for m/z 611.2 before and after oxidation (using protonated arginine at m/z 175.1 as the reference) was 3.69%. Therefore, the measured amount of rutin is 528.08 pmol, which is close to the injection amount of 500 pmol (5.62% measurement error).

Quantification for mixture analysis. In an embodiment, the quantification method is used to analyze a mixture.

Example 2

Uric acid (UA) in a raw urine sample was analyzed using the LC/EC/MS method using the same setup as in Example 1. High levels of uric acid are considered an important risk factor for patients and is also related to kidney disease, so it is crucial to determine the uric acid level in urine. As shown below, uric acid (MW 169.1) is oxidized to a diimine intermediate (MW 167.1) upon electrochemical oxidation.

A raw urine sample obtained from a male volunteer was filtered using 0.2 μm Acrodisc MS syringe filter (WWPTFE membrane) and diluted 8-fold using H$_2$O containing 0.1% formic acid. The diluted urine sample was injected into the UPLC for separation with an injection volume was 6 µL and a mobile phase flow rate of 300 µL. A voltage of +1.3 V was applied to the cell for oxidation, and the DESI solvent flow rate was 10 µL/min. The elution program was 100% to 95% in 4 min A, and 95% to 70% A in 2 min.

Figure 8A:
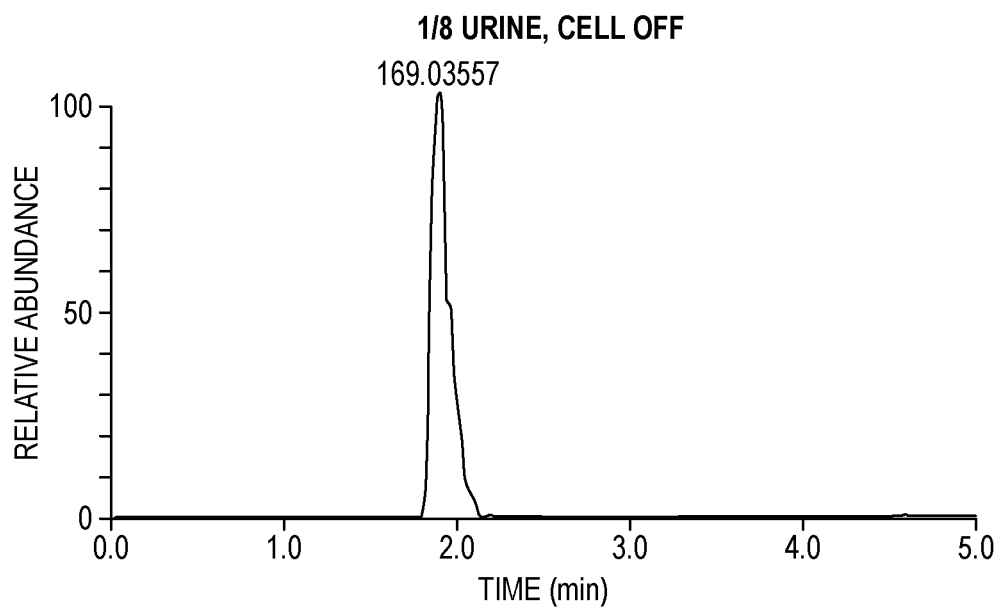
FIGS. 8A and 8B are graphs showing an extracted ion chromatogram peak for uric acid before and after electrolysis, respectively.
Figure 8B:
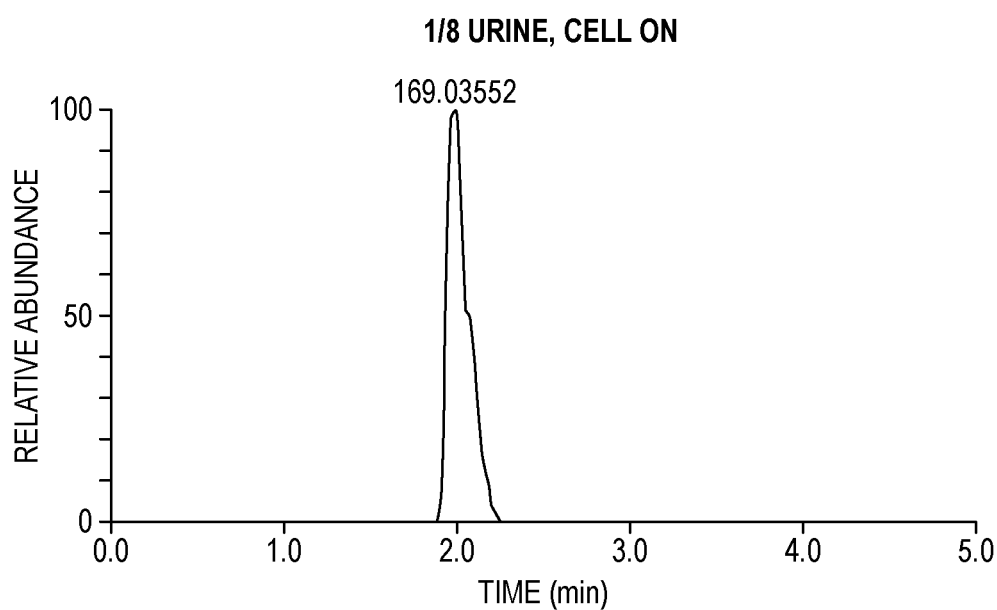
Figure 8C:
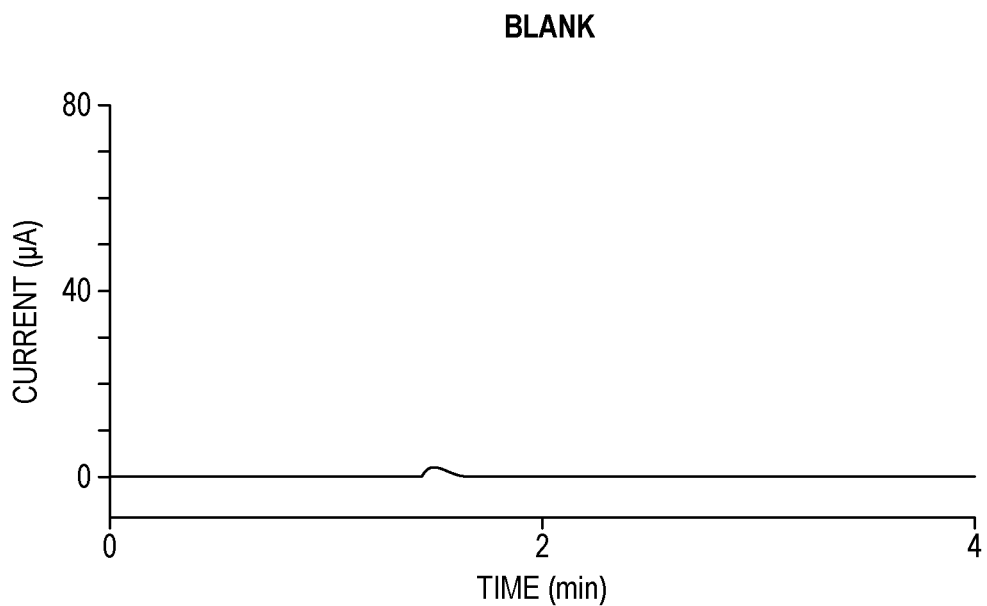
FIGS. 8C and 8D are graphs showing the electrochemical current response for a blank sample and the injected urine sample, respectively.
Figure 8D:
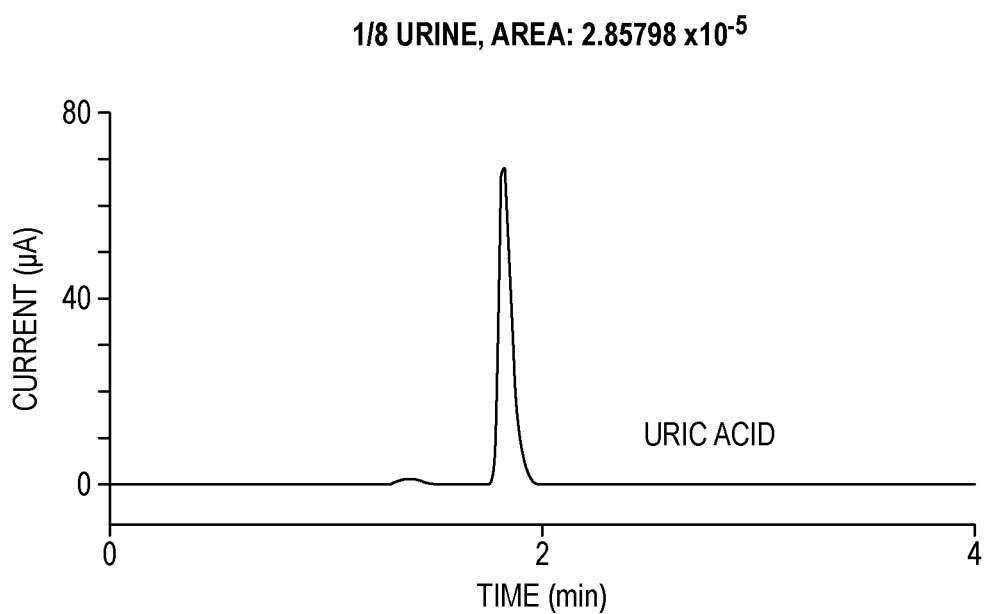

FIG. 8A displays the EIC of the uric acid peak at m/z 169 when there was no oxidation potential applied to the cell. When +1.3 V was applied to the cell for oxidation of uric acid, there was a slight decrease in the EIC peak by 8.05% (FIG. 8B). Meanwhile, when the oxidation potential was applied, an electric current response at 1.9 min was recorded as shown in FIG. 8D. This contrasts with the blank sample for which no current peak at 1.9 min was observed (FIG. 8C). The current peak integration indicates that 148.87 pmol uric acid was oxidized. Therefore, the amount of uric acid in the injected sample was calculated to be 1848 pmol. To compare, the diluted urine sample was also quantified using LC-UV, considered as "a gold standard" for quantification, employing standard uric acid as reference. The LC/UV result showed that 6 µL of the diluted urine sample contained 1860 pmol of uric acid. Therefore, the results of the LC/EC/MS method differed with the LC/UV result only by 0.64%.

Figure 9:
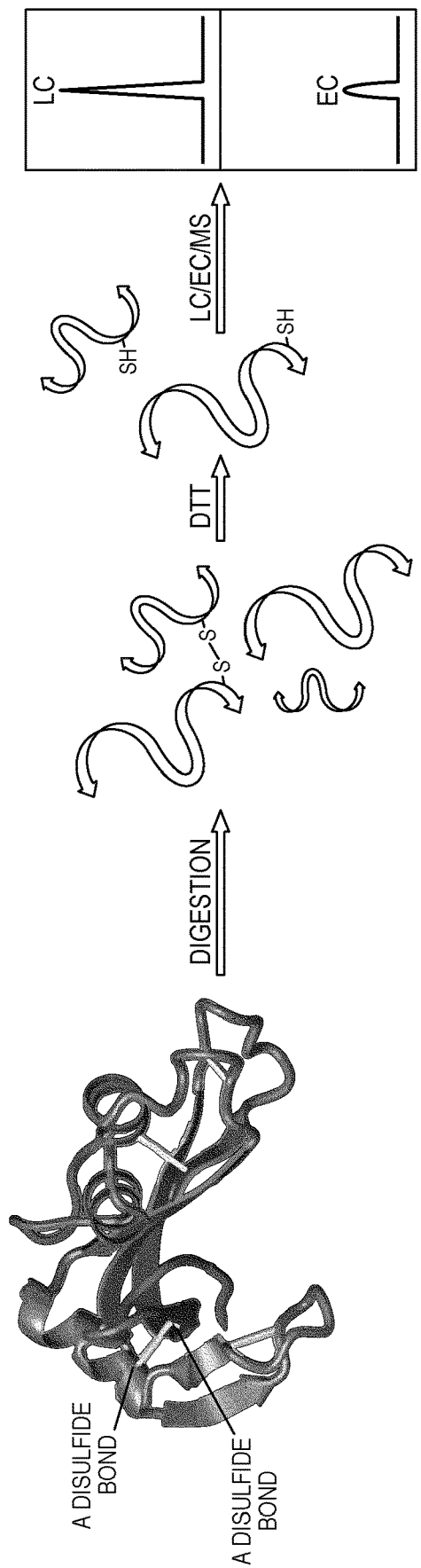
FIG. 9 is a schematic of a process for directly quantifying proteins according to another embodiment of the present invention.

Applications to protein quantification. In an embodiment, the quantification method is directly used for absolute protein quantification, particularly for a wide range of proteins containing disulfide bonds or cysteine groups (e.g., antibody drugs). As illustrated in FIG. 9, a protein containing disulfide bonds or free thiol groups can be digested into peptides that contain free thiol groups using enzymes, such as trypsin. The resulting peptide mixture can be reduced using reductants, such as dithiothreitol, and then separated by LC. LC-separated peptides containing thiol groups can be oxidized on an electrode (e.g., Au) in an electrochemical cell and subsequently online monitored by MS. The oxidation of a thiol peptide causes an electric current peak which can be integrated and provides the information how much peptide is oxidized. The percentage of the oxidation of the thiol peptide can be revealed based on the MS spectra acquired before and after electrolysis. Thus, the peptide can be quantified, which provides the quantity for its precursor target protein. The same protein quantification strategy can be applied based on the quantification of a peptide containing other redox-active amino acid residues, such as tryptophan or tyrosine residues, produced from protein digestion.

Example 3

Figure 10:
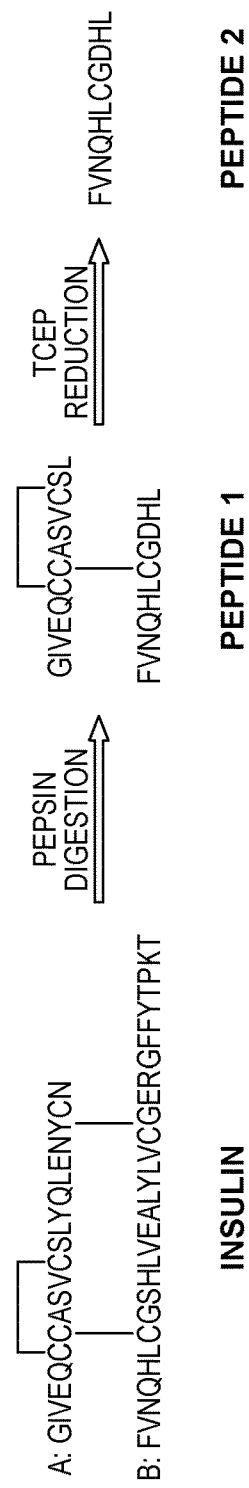
FIG. 10 is a schematic showing the formation of the peptide 2 from digestion and subsequent reduction of insulin.

Insulin is a protein containing three pairs of disulfide bonds. With reference to FIG. 10, insulin was digested by pepsin with a protein/enzyme ratio of 25:1 at 25° C. (i.e., room temperature) in water containing 1% formic acid for 12 hours. The digested insulin was further reduced with tris(2-carboxyethyl)phosphine (TCEP) with an insulin/TCEP ratio of 1:10 for 2 h. The protein was completely digested and reduced to obtain peptide 2 (sequence: FVNQHLCGDHL). Because the peptide 2 carries a free thiol (from its cysteine residue), it could undergo electrochemical oxidation to re-form a disulfide bond. The mixture was diluted to a concentration of 100 µM. The diluted sample was injected into the UPLC for separation, and the injection volume was 6 µL. The electrochemical cell was turned on at 6 minutes in order to avoid the oxidation of TCEP, so that the efficiency was maintained. A voltage of +1.3 V was applied to the cell for thiol peptide oxidation. The elution program was 95% to 90% A in 6 min, 90% to 80% A in 6 min.

Figure 11A:
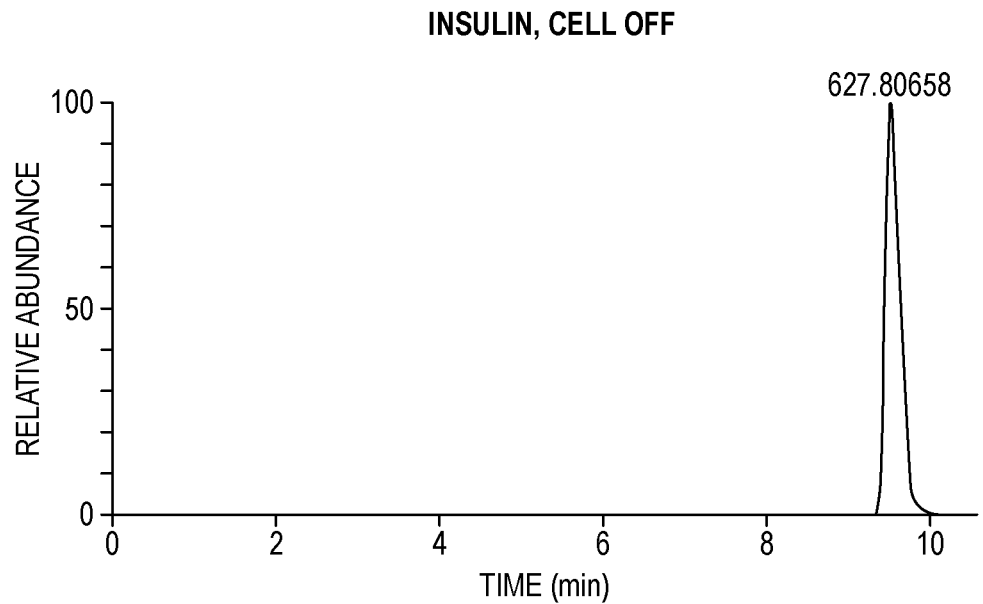
FIGS. 11A and 11B are graphs showing the extracted ion chromatogram peak of +2 ion of the peptide 2 after reduction of the insulin before and after electrolysis, respectively.
Figure 11B:
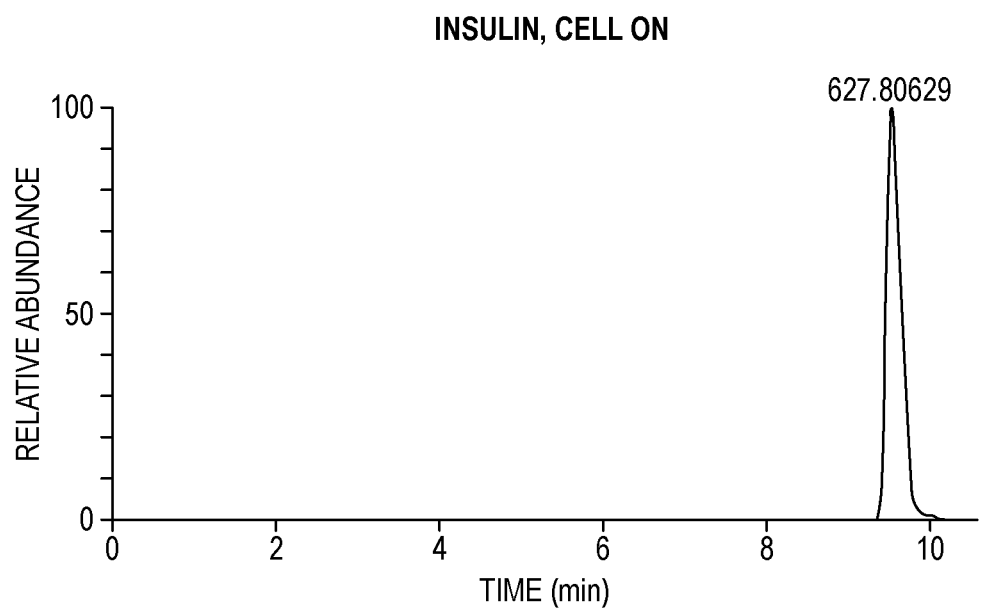

FIGS. 11A and 11B show the acquired MS spectrum (DESI spectra) when applied potential was 0 V and +1.5 V, respectively. When the digested and reduced insulin mixture was subject to LC separation, a peak at m/z 627.81 corresponding to +2 ion of the peptide 2 FVNQHLCGDHL eluted out at 9.5 min. Upon electrolysis, the EIC peak area was reduced by 2.14% (comparing the peaks shown in FIGS. 11A and 11B), indicating that 2.14% peptide 2 was oxidized. Indeed, an oxidation product ion at m/z 1253.6 was observed in the acquired MS spectra (FIG. 12A), corresponding to the peptide 2 dimer.

Figure 11C:
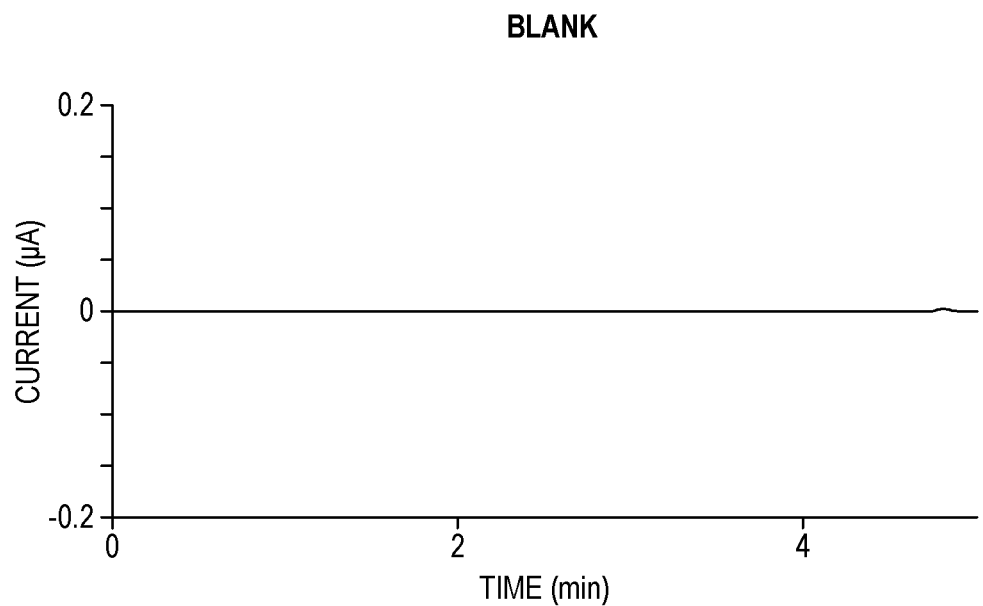
FIGS. 11C and 11D are graphs showing the electrochemical current response due to oxidation of a blank sample and the peptide 2, respectively.
Figure 11D:
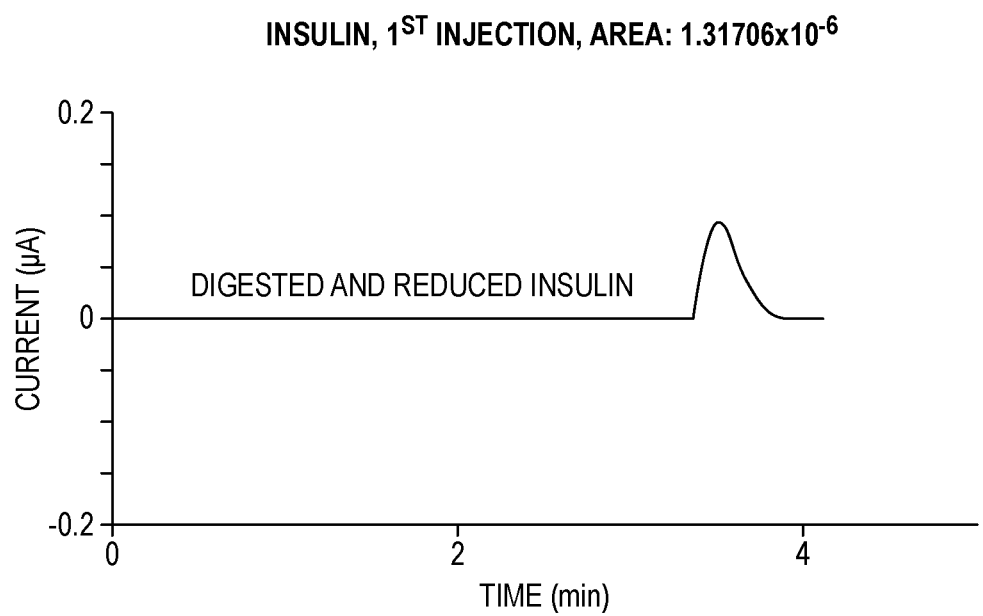

FIGS. 11C and 11D show the electric current for a blank and the digested and reduced insulin mixture, respectively. The resulting electric current was integrated by importing data point to software Origin Pro 8.0, which showed that the amount of the oxidized peptide be 12.45 pmol. Because 2.14% of the peptide 2 was reduced, the total measured amount of peptide 2 is 581 pmol, which suggests that the insulin amount is 581 pmol (1 mole of insulin theoretically produces 1 mole of the peptide 2). In comparison to the actual injection amount of 600 pmol of insulin, only 3.12% measurement error occurred, indicating a high accuracy of the quantification method.

Figure 12A:
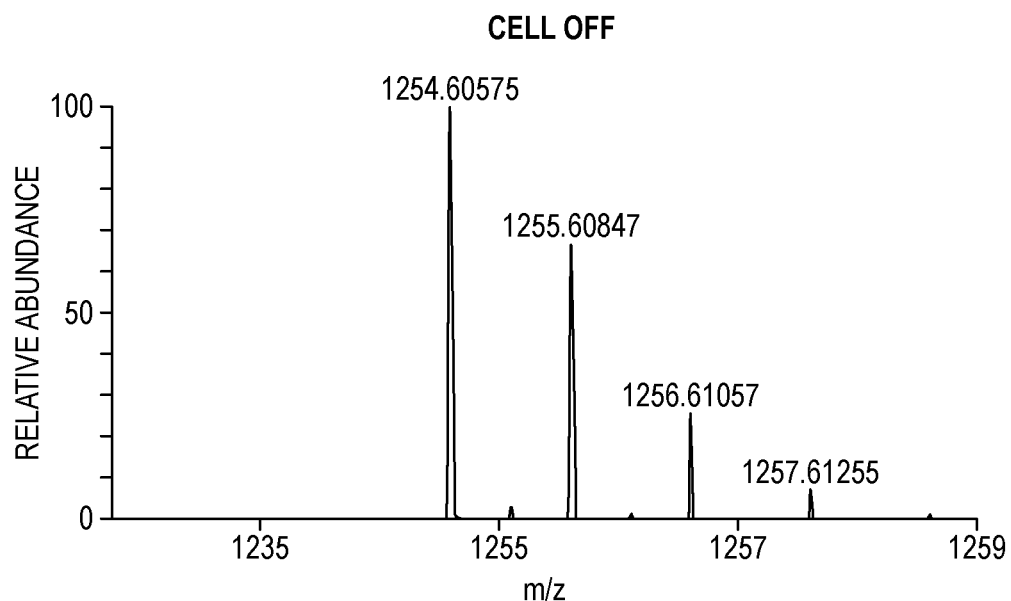
FIGS. 12A and 12B are mass spectra graphs showing the peptide 2 before and after electrochemical oxidation, respectively.
Figure 12B:
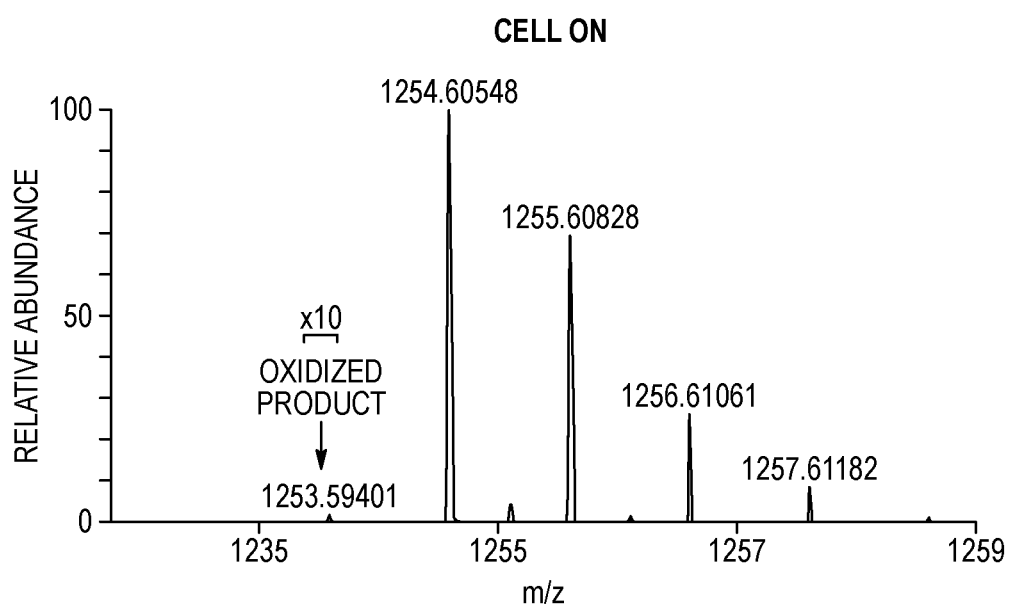

With reference to FIGS. 12A and 12B, an oxidation peak was observed at m/z 1253.6 (a), corresponding to the peptide 2 dimer bridged with a disulfide bond, FVNQHLCGDHL/FVNQHLCGDHL. The ion at m/z 1254.6 corresponds to +1 ion of the peptide 2.

This method is not limited to protein size, as a very large protein could be digested into small peptides for quantification. Again, the method does not require protein standards for quantification, which is quite advantageous as it is often difficult to obtain protein standards.

Figure 13:
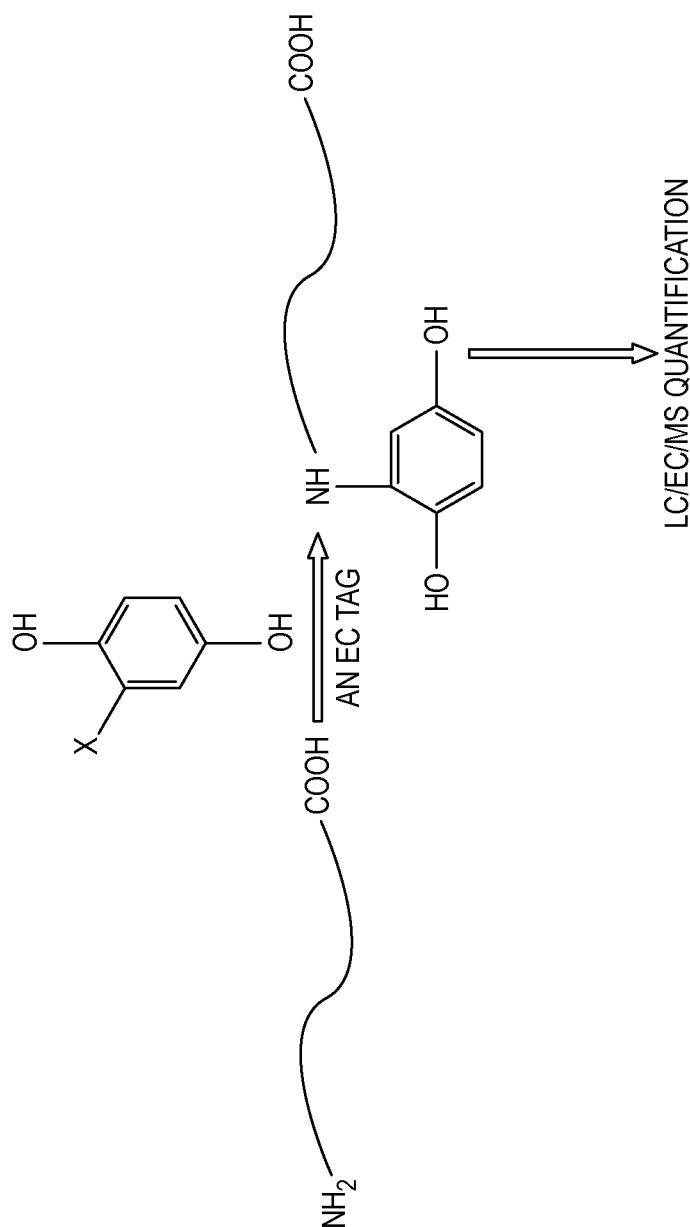
FIG. 13 is a schematic of a process for quantifying compounds that are not electrochemically active using a chemical tagging strategy according to another embodiment of the present invention.

Quantification for compounds that are not electrochemically active. In an embodiment, the quantification method is used to analyze compounds that are not electrochemically active (i.e., not oxidizable or reducible). The target molecule, which is not electrochemically active, is tagged with an electrochemical tag, such as ferrocene or a hydroquinone group. With reference to FIG. 13, a peptide that does not have thiol group is tagged with an electrochemical tag of hydroquinone. The tagged peptide is then quantified according to an embodiment of the present invention such as one described above.

While specific embodiments have been described in considerable detail to illustrate the present invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A method of quantifying a target compound in a sample comprising:
applying an oxidation/reduction potential to an electrochemical cell containing the target compound;
measuring an electrochemical current during the application of the oxidation/reduction potential;
ionizing and directing the target compound before and after the application of the oxidation/reduction potential to a mass spectrometer that measures a target compound ion intensity;

determining a target compound ion intensity change due to the application of the oxidation/reduction potential; and determining a total amount of the target compound in the sample using the measured electrochemical current and the target compound ion intensity change.

2. The method of claim 1, wherein determining the target compound ion intensity change comprises either comparing the target compound ion intensity before and after the application of the oxidation/reduction potential relative to a reference peak or comparing the integrated peak area of a target compound ion in an extracted ion chromatogram before and after the application of the oxidation/reduction potential.

3. The method of claim 2, wherein determining the target compound ion intensity change includes comparing the target compound ion intensity before and after the application of the oxidation/reduction potential relative to the reference peak, and wherein the sample includes a reference compound, the method further comprising measuring an ion intensity of the reference compound to provide the reference peak.

4. The method of claim 3, wherein the reference compound is not oxidized or reduced by the oxidation/reduction potential.

5. The method of claim 1, wherein determining the target compound ion intensity change includes using the following equation:

$$A = A_{o/r}/(\% \text{ of the target compound that is oxidized/reduced}) = A_{o/r}/(\text{the target compound ion intensity change \%})$$

where A is the total amount of the target compound in the sample, and $A_{o/r}$ is an amount of the target compound that was oxidized/reduced.

6. The method of claim 1, wherein the target compound is a protein, the method further comprising:
digesting and reducing the protein into peptides before applying the oxidation/reduction potential.

7. The method of claim 6, wherein the protein contains either disulfide bonds or cysteine groups, and the peptides contain free thiol groups.

8. The method of claim 6, wherein the protein contains either tryptophan or tyrosine residues, and the peptides contain either the tryptophan or tyrosine residues.

9. The method of claim 1, wherein the target compound is not electrochemically active, the method further comprising:
tagging the target compound with an electrochemical tag.

10. The method of claim 1, wherein determining the total amount of the target compound in the sample is accomplished without comparison to a chemical standard.

11. A device for quantifying a target compound in a sample comprising:
an electrochemical cell;
an ionizer that produces an ionized target compound;
a mass spectrometer configured to measure an ion intensity of the ionized target compound, the mass spectrometer being coupled to the electrochemical cell via the ionizer;
a sensor that monitors and records an electrochemical current during an oxidation/reduction process in the electrochemical cell; and
a controller configured to determine a target compound ion intensity change and to determine a total amount of the target compound in the sample using the recorded electrochemical current and the target compound ion intensity change.

12. The device of claim 11, wherein the ionizer involves one of electrospray ionization, desorption electrospray ionization, atmospheric pressure chemical ionization, or matrix-assisted laser desorption ionization.

13. The device of claim 11, wherein the ionizer includes an ambient ionization method using high energy particles, laser, or plasma.

14. The device of claim 11, wherein the mass spectrometer is downstream of the electrochemical cell.

15. The device of claim 11, further comprising:
a liquid chromatography separator coupled to the electrochemical cell that is configured to separate the target compound from the sample before the sample enters the electrochemical cell.

16. The device of claim 15, wherein the electrochemical cell is downstream of the liquid chromatography separator.

17. The device of claim 11, wherein the sensor is a potentiostat.

18. The device of claim 11, wherein the controller uses the following equation:

$$A = A_{o/r}/(\% \text{ of the target compound that is oxidized/reduced}) = A_{o/r}/(\text{the target compound ion intensity change \%})$$

where A is the total amount of the target compound in the sample, and $A_{o/r}$ is an amount of the target compound that was oxidized/reduced.

19. The device of claim 11, wherein the controller is configured to determine the total amount of the target compound in the sample without comparison to a chemical standard.

* * * * *

UNITED STATES PATENT AND TRADEMARK OFFICE
CERTIFICATE OF CORRECTION

| | |
|---|---|
| PATENT NO. | : 11,360,058 B2 |
| APPLICATION NO. | : 16/341622 |
| DATED | : June 14, 2022 |
| INVENTOR(S) | : Hao Chen |

It is certified that error appears in the above-identified patent and that said Letters Patent is hereby corrected as shown below:

In the Specification

Column 6, Line 16, "3.0 min" should be --3.0 min.--.

Column 7, Line 29, "FIG. 6A shows that the TIC" should be --FIG. 6A shows the TIC--.

Column 9, Line 2, "volume was 6 µL" should be --volume is 6 µL--.

In the Claims

Column 11, Line 29 (Claim 5), "A=$A_{o/r}$(% of the target" should be --A=$A_{o/r}$/(% of the target--.

Signed and Sealed this
Tenth Day of January, 2023

Katherine Kelly Vidal
*Director of the United States Patent and Trademark Office*